(12) United States Patent
Callan et al.

(10) Patent No.: US 11,607,489 B2
(45) Date of Patent: Mar. 21, 2023

(54) INJECTOR STATE LOGIC WITH HEMODYNAMIC MONITORING

(71) Applicant: BAYER HEALTHCARE LLC, Whippany, NJ (US)

(72) Inventors: Gerald Callan, Cranberry Township, PA (US); Michael Spohn, Fenelton, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 705 days.

(21) Appl. No.: 16/613,457

(22) PCT Filed: May 25, 2018

(86) PCT No.: PCT/US2018/034613
§ 371 (c)(1),
(2) Date: Nov. 14, 2019

(87) PCT Pub. No.: WO2018/218132
PCT Pub. Date: Nov. 29, 2018

(65) Prior Publication Data
US 2020/0330682 A1 Oct. 22, 2020

Related U.S. Application Data

(60) Provisional application No. 62/511,471, filed on May 26, 2017.

(51) Int. Cl.
*A61M 5/168* (2006.01)
*G16H 20/17* (2018.01)
(Continued)

(52) U.S. Cl.
CPC ........ *A61M 5/16804* (2013.01); *A61M 5/007* (2013.01); *G16H 20/17* (2018.01);
(Continued)

(58) Field of Classification Search
CPC .............. A61M 5/007; A61M 5/14216; A61M 5/16854; A61M 5/1723; A61M 5/365; A61B 5/0205; A61B 5/026; A61B 6/504
See application file for complete search history.

(56) References Cited

U.S. PATENT DOCUMENTS 1,832,266 A  11/1931 Thomas
2,191,990 A   2/1940 Jordan
(Continued)

FOREIGN PATENT DOCUMENTS

DE  202005015741 U1  12/2005
EP       1090650 A1   4/2001
(Continued)

OTHER PUBLICATIONS

Hemodynamic Monitoring: Principles to Practice—M. L. Cheatham, MD, FACS, FCCM, Revised on Jan. 13, 2009.
(Continued)

*Primary Examiner* — Manuel A Mendez
(74) *Attorney, Agent, or Firm* — Joseph L. Kent; James R. Stevenson; David Schramm

(57) ABSTRACT

A fluid injection system including a graphical user interface, a fluid control module operatively connected to the graphical user interface, a monitoring control module provided in at least one of the graphical user interface and the fluid control module, a fluid injector operatively connected to the graphical user interface and the fluid control module, at least one fluid path set in fluid communication with the fluid control module, and a hemodynamic monitoring system operatively connected to the fluid path set and the monitoring control module. The hemodynamic monitoring system may be configured to receive electrical signals regarding pressure waves formed in medical fluid directed through the fluid path set based on a location of the fluid path set in a patient's vasculature, to convert the electrical signals to pressure
(Continued)

wave form information, and to send the pressure wave form information to the monitoring control module.

18 Claims, 4 Drawing Sheets

(51) Int. Cl.
  *G16H 40/67* (2018.01)
  *A61M 5/00* (2006.01)
  *A61B 6/00* (2006.01)
  *A61M 5/14* (2006.01)

(52) U.S. Cl.
  CPC .............. *G16H 40/67* (2018.01); *A61B 6/481* (2013.01); *A61B 6/504* (2013.01); *A61M 2005/1402* (2013.01); *A61M 2005/1403* (2013.01); *A61M 2205/3337* (2013.01); *A61M 2205/505* (2013.01); *A61M 2230/30* (2013.01)

(56) References Cited

U.S. PATENT DOCUMENTS

| | | |
|---|---|---|
| 2,202,123 A | 5/1940 | Strode |
| 2,223,944 A | 12/1940 | Roy |
| 2,415,258 A | 2/1947 | Parker et al. |
| 2,702,547 A | 2/1955 | Glass |
| 2,729,228 A | 1/1956 | Stevenson |
| 3,207,179 A | 9/1965 | Klagues |
| 3,565,056 A | 2/1971 | Louis |
| 3,633,605 A | 1/1972 | Larry |
| 3,645,139 A | 2/1972 | John |
| 3,675,891 A | 7/1972 | Gordon et al. |
| 3,713,341 A | 1/1973 | Madsen et al. |
| 3,831,629 A | 8/1974 | Mackal et al. |
| 3,859,985 A | 1/1975 | Eckhart |
| 3,863,504 A | 2/1975 | Borsanyi |
| 3,865,100 A | 2/1975 | Kanai et al. |
| 4,005,219 A | 1/1977 | Buckle et al. |
| 4,005,710 A | 2/1977 | Zeddies et al. |
| 4,077,882 A | 3/1978 | Gangemi |
| 4,080,967 A | 3/1978 | O"Leary |
| 4,094,318 A | 6/1978 | Burke et al. |
| 4,109,535 A | 8/1978 | Reed et al. |
| 4,226,124 A | 10/1980 | Kersten |
| 4,243,031 A | 1/1981 | Genese |
| 4,314,480 A | 2/1982 | Becker |
| 4,331,262 A | 5/1982 | Snyder et al. |
| 4,335,729 A | 6/1982 | Reynolds et al. |
| 4,337,770 A | 7/1982 | Young et al. |
| 4,341,224 A | 7/1982 | Stevens |
| 4,342,218 A | 8/1982 | Fox |
| 4,351,332 A | 9/1982 | Whitney et al. |
| 4,384,470 A | 5/1983 | Fiore |
| 4,392,847 A | 7/1983 | Whitney et al. |
| 4,414,999 A | 11/1983 | Basta |
| 4,415,003 A | 11/1983 | Paradis et al. |
| 4,428,383 A | 1/1984 | Devroom |
| 4,431,009 A | 2/1984 | Marino, Jr. et al. |
| 4,444,198 A | 4/1984 | Petre |
| 4,444,219 A | 4/1984 | Hollenstein |
| 4,464,172 A | 8/1984 | Lichtenstein |
| 4,509,946 A | 4/1985 | McFarlane |
| 4,516,595 A | 5/1985 | Acomb |
| 4,517,844 A | 5/1985 | Powell |
| 4,610,256 A | 9/1986 | Wallace |
| 4,624,662 A | 11/1986 | Le |
| 4,677,980 A | 7/1987 | Reilly et al. |
| 4,683,916 A | 8/1987 | Raines |
| 4,697,617 A | 10/1987 | Bourke et al. |
| 4,712,583 A | 12/1987 | Pelmulder et al. |
| 4,779,625 A | 10/1988 | Cole |
| 4,815,313 A | 3/1989 | Beard |
| 4,838,856 A | 6/1989 | Mulreany et al. |
| 4,858,127 A | 8/1989 | Kron et al. |
| 4,890,640 A | 1/1990 | King, Sr. |
| 4,960,127 A | 10/1990 | Noce et al. |
| 5,002,528 A | 3/1991 | Palestrant |
| 5,004,079 A | 4/1991 | Ivers et al. |
| 5,007,904 A | 4/1991 | Densmore et al. |
| 5,057,081 A | 10/1991 | Sunderland et al. |
| 5,076,280 A | 12/1991 | Moriuchi et al. |
| 5,106,379 A | 4/1992 | Leap |
| 5,120,313 A | 6/1992 | Elftman |
| 5,140,862 A | 8/1992 | Pappalardo |
| 5,148,811 A | 9/1992 | Messinger |
| 5,174,038 A | 12/1992 | Neyens et al. |
| 5,237,999 A | 8/1993 | Von Berg |
| 5,241,986 A | 9/1993 | Yie |
| 5,263,367 A | 11/1993 | Pippert |
| 5,273,047 A | 12/1993 | Tripp et al. |
| 5,300,031 A | 4/1994 | Neer et al. |
| 5,336,051 A | 8/1994 | Tamari |
| 5,383,858 A | 1/1995 | Reilly et al. |
| 5,423,751 A | 6/1995 | Harrison et al. |
| 5,429,611 A | 7/1995 | Rait |
| 5,433,712 A | 7/1995 | Stiles et al. |
| 5,460,609 A | 10/1995 | O'Donnell |
| 5,515,851 A | 5/1996 | Goldstein |
| 5,535,785 A | 7/1996 | Werge et al. |
| 5,540,668 A | 7/1996 | Wilson, Jr. et al. |
| 5,551,301 A | 9/1996 | Cowan |
| 5,554,113 A | 9/1996 | Novak et al. |
| 5,569,208 A | 10/1996 | Woelpper et al. |
| 5,573,515 A | 11/1996 | Wilson et al. |
| 5,575,767 A | 11/1996 | Stevens |
| 5,584,671 A | 12/1996 | Schweitzer, Jr. et al. |
| 5,593,385 A | 1/1997 | Harrison et al. |
| 5,630,935 A | 5/1997 | Treu |
| 5,631,552 A | 5/1997 | Ogawa et al. |
| 5,684,246 A | 11/1997 | Korpi |
| 5,692,539 A | 12/1997 | Pickl, Jr. |
| 5,727,594 A | 3/1998 | Choksi |
| 5,770,675 A | 6/1998 | Kim et al. |
| 5,775,671 A | 7/1998 | Cote, Sr. |
| 5,779,675 A | 7/1998 | Reilly et al. |
| 5,800,397 A | 9/1998 | Wilson et al. |
| 5,808,203 A | 9/1998 | Nolan, Jr. et al. |
| 5,840,026 A | 11/1998 | Uber, III et al. |
| 5,873,861 A | 2/1999 | Hitchins et al. |
| 5,916,165 A | 6/1999 | Duchon et al. |
| 5,938,639 A | 8/1999 | Reilly et al. |
| 5,947,935 A | 9/1999 | Kazousky et al. |
| 5,967,176 A | 10/1999 | Blann et al. |
| 5,992,462 A | 11/1999 | Atkinson et al. |
| 6,029,076 A | 2/2000 | Fiddian-Greene et al. |
| 6,089,272 A | 7/2000 | Brand et al. |
| 6,096,011 A | 8/2000 | Trombley, III et al. |
| 6,099,502 A | 8/2000 | Duchon et al. |
| 6,099,511 A | 8/2000 | Devos et al. |
| 6,171,253 B1 | 1/2001 | Bullister et al. |
| 6,221,045 B1 | 4/2001 | Duchon et al. |
| 6,336,913 B1 | 1/2002 | Spohn et al. |
| 6,344,030 B1 | 2/2002 | Duchon et al. |
| 6,346,084 B1 | 2/2002 | Schnell et al. |
| 6,390,120 B1 | 5/2002 | Guala |
| 6,390,130 B1 | 5/2002 | Guala |
| 6,422,057 B1 | 7/2002 | Anderson |
| 6,471,674 B1 | 10/2002 | Emig et al. |
| 6,475,192 B1 | 11/2002 | Reilly et al. |
| 6,536,278 B1 | 3/2003 | Scagliarini |
| 6,595,957 B1 | 7/2003 | Griffiths et al. |
| 6,622,752 B2 | 9/2003 | Kushida et al. |
| 6,626,862 B1 | 9/2003 | Duchon et al. |
| 6,649,046 B2 | 11/2003 | Chevallet |
| 6,650,929 B1 | 11/2003 | Nemoto et al. |
| 6,656,157 B1 | 12/2003 | Duchon et al. |
| 6,811,139 B2 | 11/2004 | Hishikawa |
| 6,866,039 B1 | 3/2005 | Wright et al. |
| 6,866,654 B2 | 3/2005 | Callan et al. |
| 6,896,002 B2 | 5/2005 | Hart et al. |
| 6,929,619 B2 | 8/2005 | Fago et al. |
| 6,945,959 B2 | 9/2005 | Duchon et al. |
| 6,986,753 B2 | 1/2006 | Bui |

(56) References Cited

U.S. PATENT DOCUMENTS

| | | |
|---|---|---|
| 6,988,510 B2 | 1/2006 | Enerson |
| 7,014,624 B2 | 3/2006 | Meythaler et al. |
| 7,017,418 B1 | 3/2006 | Thakre et al. |
| 7,094,216 B2 | 8/2006 | Trombley, III et al. |
| 7,153,288 B2 | 12/2006 | Duchon et al. |
| 7,192,416 B1 | 3/2007 | Lazzaro et al. |
| 7,267,667 B2 | 9/2007 | Hou et al. |
| 7,291,131 B2 | 11/2007 | Call |
| 7,302,960 B2 | 12/2007 | Patzer |
| 7,326,186 B2 | 2/2008 | Trombley et al. |
| 7,389,788 B2 | 6/2008 | Wilson et al. |
| 7,549,977 B2 | 6/2009 | Schriver et al. |
| 7,556,619 B2 | 7/2009 | Spohn et al. |
| 7,563,249 B2 | 7/2009 | Schriver et al. |
| 7,610,936 B2 | 11/2009 | Spohn et al. |
| 7,611,503 B2 | 11/2009 | Spohn et al. |
| 7,704,236 B2 | 4/2010 | Denolly |
| 7,713,239 B2 | 5/2010 | Uber et al. |
| 8,147,464 B2 | 4/2012 | Spohn et al. |
| 8,251,092 B2 | 8/2012 | Spohn et al. |
| 8,337,456 B2 | 12/2012 | Schriver et al. |
| 8,361,040 B2 | 1/2013 | Spohn et al. |
| 8,540,698 B2 | 9/2013 | Spohn et al. |
| 9,433,730 B2 | 9/2016 | Schriver et al. |
| 9,808,571 B2 | 11/2017 | Riley et al. |
| 9,895,527 B2 | 2/2018 | Spohn et al. |
| 2002/0016569 A1 | 2/2002 | Critchlow et al. |
| 2002/0143294 A1 | 10/2002 | Duchon et al. |
| 2003/0004463 A1 | 1/2003 | Reilly et al. |
| 2003/0011135 A1 | 1/2003 | Meacham |
| 2003/0011136 A1 | 1/2003 | Ramirez et al. |
| 2003/0040723 A1 | 2/2003 | Hart et al. |
| 2003/0139706 A1 | 7/2003 | Gray |
| 2003/0171712 A1 | 9/2003 | Critchlow et al. |
| 2004/0064041 A1 | 4/2004 | Lazzaro et al. |
| 2004/0122370 A1 | 6/2004 | Joyce et al. |
| 2004/0138641 A1 | 7/2004 | Patzer |
| 2004/0143212 A1 | 7/2004 | Trombley et al. |
| 2004/0143225 A1 | 7/2004 | Callan et al. |
| 2004/0158205 A1 | 8/2004 | Savage et al. |
| 2004/0168530 A1 | 9/2004 | Adolfs et al. |
| 2004/0217315 A1 | 11/2004 | Doyle |
| 2004/0221904 A1 | 11/2004 | Usher et al. |
| 2004/0254533 A1 | 12/2004 | Schriver et al. |
| 2005/0077225 A1 | 4/2005 | Usher et al. |
| 2005/0104444 A1 | 5/2005 | Callan et al. |
| 2005/0113754 A1 | 5/2005 | Cowan |
| 2005/0148867 A1* | 7/2005 | Neer ................ A61M 5/14546 600/431 |
| 2005/0194047 A1 | 9/2005 | Bausmith et al. |
| 2005/0230575 A1 | 10/2005 | Zelenski et al. |
| 2005/0234407 A1 | 10/2005 | Spohn et al. |
| 2005/0234428 A1 | 10/2005 | Spohn et al. |
| 2006/0009699 A1 | 1/2006 | Roteliuk et al. |
| 2006/0065873 A1 | 3/2006 | Doyle |
| 2006/0079765 A1 | 4/2006 | Neer et al. |
| 2006/0108555 A1 | 5/2006 | Kiehne |
| 2006/0149189 A1 | 7/2006 | Diamond et al. |
| 2006/0155248 A1 | 7/2006 | Hashimoto et al. |
| 2006/0178632 A1 | 8/2006 | Trombley et al. |
| 2006/0180202 A1 | 8/2006 | Wilson et al. |
| 2007/0106208 A1 | 5/2007 | Uber et al. |
| 2007/0161970 A1 | 7/2007 | Spohn et al. |
| 2008/0045919 A1 | 2/2008 | Jakob et al. |
| 2008/0086087 A1 | 4/2008 | Spohn et al. |
| 2008/0154214 A1 | 6/2008 | Spohn et al. |
| 2009/0216192 A1 | 8/2009 | Schriver et al. |
| 2011/0190710 A1 | 8/2011 | Miyoshi et al. |
| 2012/0123257 A1 | 5/2012 | Stokes, Jr. et al. |
| 2012/0130236 A1 | 5/2012 | Nystrom |
| 2013/0123619 A1 | 5/2013 | Griggs |
| 2013/0197883 A1 | 8/2013 | Grow et al. |
| 2013/0255390 A1* | 10/2013 | Riley .................... G01L 11/025 73/705 |
| 2014/0034169 A1 | 2/2014 | Harton et al. |

FOREIGN PATENT DOCUMENTS

| | | |
|---|---|---|
| EP | 1602388 A1 | 12/2005 |
| EP | 1602388 B1 | 11/2009 |
| FR | 2848859 A1 | 6/2004 |
| GB | 2274148 A | 7/1994 |
| JP | H01147841 A | 6/1989 |
| JP | H0630905 A | 2/1994 |
| JP | H07100212 A | 4/1995 |
| JP | 2004357985 A | 12/2004 |
| JP | 2010538761 A | 12/2010 |
| WO | 9308454 A1 | 4/1993 |
| WO | 9422686 A1 | 10/1994 |
| WO | 9522280 A1 | 8/1995 |
| WO | 9707841 A2 | 3/1997 |
| WO | 0010629 A1 | 3/2000 |
| WO | 0065984 A1 | 11/2000 |
| WO | 0204049 A1 | 1/2002 |
| WO | 2005110007 A2 | 11/2005 |
| WO | 2007146586 A2 | 12/2007 |
| WO | 2011041290 A1 | 4/2011 |
| WO | 2012155035 A1 | 11/2012 |
| WO | 2015061723 A2 | 4/2015 |

OTHER PUBLICATIONS

"International Preliminary Report on Patentability in PCT Application No. PCT/US2018/034613", dated Dec. 5, 2019.

Omron. 7 Series Blook Pressure Monitor with ComFit Cuff. Instruction Manual. 2010.

OMRON Instruction Manual, 7 series, Blood Pressure Monitor with ComFit Cuff, 2010.

* cited by examiner

INJECTOR STATE LOGIC WITH HEMODYNAMIC MONITORING

CROSS-REFERENCE TO RELATED APPLICATIONS

This application is a 371 national phase application of PCT International Application No. PCT/US2018/034613, filed May 25, 2018, and claims the priority to U.S. Provisional Patent Application No. 62/511,471, filed on May 26, 2017, the disclosures of which are incorporated herein by reference in their entirety.

BACKGROUND

Field of the Technology

The present disclosure relates, generally, to fluid injector state logic systems and, more particularly, to fluid injector state logic systems with hemodynamic monitoring.

Description of Related Art

Angiography is a procedure used in the detection and treatment of abnormalities or restrictions in blood vessels. During angiography, a radiographic image of a vascular structure (i.e., blood vessel) is obtained by injecting radiographic contrast material, also referred to as contrast media or simply "contrast," through a catheter into a vein or artery of the patient. X-rays are passed through the region of the body in which the contrast media is concentrated. The X-rays are absorbed by the contrast material, causing a radiographic outline or image of the blood vessel containing the contrast media. The X-ray images of the blood vessel filled with the contrast media are usually recorded onto film, videotape, and/or digital media and may be displayed on a monitor.

Many angiographic procedures, in particular coronary angiography and especially coronary vascular interventional procedures such as angioplasty, require frequent intermittent injections of contrast media. The contrast media is administered in varying volumes as well as modulated strengths and time durations. The intermittent contrast media injections are critical for optimal positioning of guiding catheters at the targeted blood vessels, positioning of guide wires to and through the targeted areas during catheter interventions (i.e., percutaneous transluminal coronary angioplasty), and for assessment of the results of such interventional procedures.

During angiography, after a physician places the angiographic catheter into a vein or artery, the angiographic catheter is connected to either a manual or automatic contrast medium injection mechanism. A typical manual contrast media injection mechanism includes a syringe and a catheter connection. The user of the manual contrast media injection mechanism adjusts the rate and volume of injection by altering the manual actuation force applied to the plunger of the syringe.

Automatic contrast media injection mechanisms typically involve a syringe connected to an injector having a linear actuator. The liner actuator is connected to a motor that is controlled electronically, for example by a control module. The operator enters into the electronic control module information regarding fixed volumes of contrast media and fixed rates of injection to be used over the course of the angiography procedure. A change in flow rate may be affected by stopping the mechanism and resetting the parameters. Recent improvements in the radiographic imaging field have applied software and hardware interfaces to automatic contrast media injection mechanisms to provide variable flow rate and fixed flow rate modes to the operator. Additionally, the delivery of common flushing agents, such as saline, may also be controlled using the software/hardware interfaces.

While many protective features have been incorporated into the software/hardware interfaces for the automatic contrast media injection systems, unintentional errors by the attending physicians, technicians, or nurses can cause injury to a patient. In particular, one potential issue associated with automatic contrast media injection procedures is unintentional injection of air into arterial vasculature of a patient. Accidental misuse of the automatic contrast media injection system by the operator can initiate injector states or actions, such as purging or priming the fluid lines, while the patient is still connected to the automatic contrast media injection system. The accidental initiation of the priming or purging stage may deliver unwanted volumes of air into the patient's arterial vasculature. Methods and injector systems that may prevent inadvertent errors during injection procedures would be advantageous.

BRIEF SUMMARY

In view of the foregoing, there is a current need for a fluid injector state logic system that notifies a physician or otherwise recognizes when a patient is still fluidly connected to an automatic contrast media injection system. There is a further need for a fluid injector state logic system that prevents activation of an injector state, such as purging or priming, until the physician has verified that the patient is not fluidly connected to the automatic contrast media injection system or the catheter line has already been purged or primed before connection to the patient.

In one example, a fluid injection system may include a graphical user interface, a fluid control module operatively connected to the graphical user interface, at least one monitoring control module operatively connected to at least one of the graphical user interface and the fluid control module, a fluid injector operatively connected to the graphical user interface and the fluid control module, at least one fluid path set in fluid communication with the fluid control module, and a hemodynamic monitoring system operatively connected to the fluid path set and the monitoring control module. The hemodynamic monitoring system may be configured to receive electrical signals indicative of pressure waves formed in a medical fluid injected through the fluid path set using the fluid injector based on a location of the fluid path set in a patient's vasculature, to convert the electrical signals to pressure wave form information, and to send the pressure wave form information to the monitoring control module. Based on the pressure wave form information received from the hemodynamic monitoring system, the monitoring control module may be configured to create a state logic protocol to control the fluid control module to allow an injection procedure or allow a priming or purging sequence based on the pressure wave form information.

In another example, the state logic protocol created by the monitoring control module may include, in the event the pressure wave information is indicative of fluid communication between the fluid path set and the patient's vasculature, instructing the fluid control module to allow the injection procedure, while preventing the purging or priming sequence, and, in the event the pressure wave information is indicative of no fluid communication between the fluid path set and the patient's vasculature, instructing the fluid control module to allow the purging or priming sequence. A transducer may be positioned in-line with the fluid path set and operatively connected to the hemodynamic monitoring system. The transducer may be configured to monitor and convert a fluid flow pressure of the medical fluid within the fluid path set into the electrical signals to be sent to the hemodynamic monitoring system. The transducer may be a pressure transducer. A hemodynamic monitoring mechanism may be positioned in-line between the transducer and the hemodynamic monitoring system. The hemodynamic monitoring mechanism may be configured to send pressure wave form information regarding the medical fluid in the fluid path set to the monitoring control module. The graphical user interface may include a first monitoring control module and the fluid control module may include a second monitoring control module. An automatic pressure isolation valve may be positioned in-line with the fluid path set. The automatic pressure isolation valve may be configured to control the flow of the medical fluid through the fluid path set. The graphical user interface may be configured to display the pressure wave form information to a user to indicate whether there is a fluctuation in the fluid pressure in the fluid path set. In the event the medical fluid is being directed through the fluid path set to the patient's vasculature, the graphical user display may display a first pressure wave, in the event the medical fluid is not being directed through the fluid path set to the patient's vasculature, the graphical user display may display a second pressure wave of substantially zero value, and in the event the medical fluid is being directed through the fluid path set with an amount of air, the graphical user display may display a third pressure wave smaller than the first pressure wave but greater than the second pressure wave. The graphical user interface may be configured to display a visual indicator regarding a status of the system. The visual indicator may be displayed as a warning indicator when a measured fluid pressure in the fluid path set is greater than a possible human intra-coronary pressure range. The visual indicator may be displayed as a caution indicator when the measured fluid pressure in the fluid path set is greater than a normal human intra-coronary pressure range, but within the possible human intra-coronary pressure range. The visual indicator may be displayed as a ready-to-use indicator when the measured fluid pressure in the fluid path set is within the normal human intra-coronary pressure range. An air detector may be positioned in-line with the at least one fluid path set.

In another example, a fluid injection system may include a fluid control module, a first fluid path set in fluid communication with the fluid control module, a second fluid path set in fluid communication with the fluid control module, a pressure isolation valve in fluid communication with the first and second fluid path sets, a third fluid path set in fluid communication with the fluid control module and a patient's vasculature, and a hemodynamic monitoring system operatively connected to the second fluid path set and the fluid control module. The hemodynamic monitoring system may be configured to receive electrical signals indicative of pressure waves formed in a medical fluid injected through the second fluid path set based on a location of the third fluid path set in a patient's vasculature, to convert the electrical signals to pressure wave form information, and to send the pressure wave form information to the fluid control module. Based on the pressure wave form information received from the hemodynamic monitoring system, the fluid control module may be configured to create a state logic protocol to allow an injection procedure or allow a purging or priming sequence using the fluid control module.

In another example, the state logic protocol created by the fluid control module may include, in the event the pressure wave information is indicative of fluid communication between the third fluid path set and the patient's vasculature, instructing the fluid control module to allow the injection procedure, while preventing the purging or priming sequence, and, in the event the pressure wave information is indicative of no fluid communication between the third fluid path set and the patient's vasculature, instructing the fluid control module to allow the purging or priming sequence. The pressure isolation valve may include an automatic spring-biased spool valve. A transducer may be positioned in-line with the second fluid path set. The transducer may be configured to monitor and convert a fluid flow pressure of the medical fluid within the second fluid path set into the electrical signals to be sent to the hemodynamic monitoring system. A hemodynamic monitoring mechanism may be positioned in-line between the transducer and the hemodynamic monitoring system. An air detector may be positioned in-line with the third fluid path set.

In another example, a method of monitoring fluid pressure within a fluid injection system may include directing a medical fluid through a fluid path set of the fluid injection system; measuring a fluid pressure of the medical fluid using a transducer positioned in-line with the fluid path set; sending fluid pressure information from the transducer to a hemodynamic monitoring system; converting the fluid pressure information into pressure wave form information using the hemodynamic monitoring system; sending the pressure wave form information to a fluid control module of the fluid injection system; and allowing an injection procedure or allowing a priming sequence, and/or a purging sequence using the fluid control module based on the pressure wave form information. The method may further include displaying the pressure wave information on a graphical user interface of the fluid injection system.

The present disclosure is also defined by the following clauses:

Clause 1: A fluid injection system, comprising: a graphical user interface; a fluid control module operatively connected to the graphical user interface; at least one monitoring control module operatively connected to at least one of the graphical user interface and the fluid control module; a fluid injector operatively connected to the graphical user interface and the fluid control module; at least one fluid path set in fluid communication with the fluid control module; and a hemodynamic monitoring system operatively connected to the fluid path set and the monitoring control module, wherein the hemodynamic monitoring system is configured to receive electrical signals indicative of pressure waves formed in a medical fluid injected through the fluid path set using the fluid injector based on a location of the fluid path set in a patient's vasculature, to convert the electrical signals into pressure wave form information, and to send the pressure wave form information to the monitoring control module, and wherein, based on the pressure wave form information received from the hemodynamic monitoring system, the monitoring control module is configured to create a state logic protocol to control the fluid control module to allow an injection procedure or allow a purging or priming sequence based on the pressure wave form information.

Clause 2: The fluid injection system as recited in Clause 1, wherein the state logic protocol created by the monitoring control module comprises: in the event the pressure wave information is indicative of fluid communication between the fluid path set and the patient's vasculature, instructing the fluid control module to allow the injection procedure, while preventing the purging or priming sequence; and in the event the pressure wave information is indicative of no fluid communication between the fluid path set and the patient's vasculature, instructing the fluid control module to allow the purging or priming sequence.

Clause 3: The fluid injection system as recited in Clause 1 or 2, further comprising a transducer positioned in-line with the fluid path set and operatively connected to the hemodynamic monitoring system, wherein the transducer is configured to monitor and convert a fluid flow pressure of the medical fluid within the fluid path set into the electrical signals to be sent to the hemodynamic monitoring system.

Clause 4: The fluid injection system as recited in Clause 3, wherein the transducer comprises a pressure transducer.

Clause 5: The fluid injection system as recited in Clause 3 or 4, further comprising a hemodynamic monitoring mechanism positioned in-line between the transducer and the hemodynamic monitoring system.

Clause 6: The fluid injection system as recited in Clause 5, wherein the hemodynamic monitoring mechanism is configured to send pressure wave form information regarding the medical fluid in the fluid path set to the monitoring control module.

Clause 7: The fluid injection system as recited in any one of Clauses 1-6, wherein the graphical user interface includes a first monitoring control module and the fluid control module includes a second monitoring control module.

Clause 8: The fluid injection system as recited in any of Clauses 1-6, further comprising an automatic pressure isolation valve positioned in-line with the fluid path set, wherein the automatic pressure isolation valve is configured to control the flow of the medical fluid through the fluid path set.

Clause 9: The fluid injection system as recited in any of Clauses 1-8, wherein the graphical user interface is configured to display the pressure wave form information to a user to indicate whether there is a fluctuation in the fluid pressure in the fluid path set.

Clause 10: The fluid injection system as recited in any of Clauses 1-9, wherein: in the event the medical fluid is being directed through the fluid path set to the patient's vasculature, the graphical user display will display a first pressure wave, in the event the medical fluid is not being directed through the fluid path set to the patient's vasculature, the graphical user display will display a second pressure wave of substantially zero value, and in the event the medical fluid is being directed through the fluid path set with an amount of air, the graphical user display will display a third pressure wave smaller than the first pressure wave but greater than the second pressure wave.

Clause 11: The fluid injection system as recited in any of Clauses 1-10, wherein the graphical user interface is configured to display a visual indicator regarding a status of the system, wherein, the visual indicator is displayed as a warning indicator when a measured fluid pressure in the fluid path set is greater than a possible human intra-coronary pressure range, wherein the visual indicator is displayed as a caution indicator when the measured fluid pressure in the fluid path set is greater than a normal human intra-coronary pressure range, but within the possible human intra-coronary pressure range, and wherein the visual indicator is displayed as a ready-to-use indicator when the measured fluid pressure in the fluid path set is within the normal human intra-coronary pressure range.

Clause 12: The fluid injection system as recited in any of Clauses 1-11, further comprising an air detector positioned in-line with the at least one fluid path set.

Clause 13: A fluid injection system, comprising: a fluid control module; a first fluid path set in fluid communication with the fluid control module; a second fluid path set in fluid communication with the fluid control module; a pressure isolation valve in fluid communication with the first and second fluid path sets; a third fluid path set in fluid communication with the pressure isolation valve and a patient's vasculature; and a hemodynamic monitoring system operatively connected to the second fluid path set and the fluid control module, wherein the hemodynamic monitoring system is configured to receive electrical signals indicative of pressure waves formed in a medical fluid injected through the second fluid path set based on a location of the third fluid path set in a patient's vasculature, to convert the electrical signals into pressure wave form information, and to send the pressure wave form information to the fluid control module, and wherein, based on the pressure wave form information received from the hemodynamic monitoring system, the fluid control module is configured to create a state logic protocol to allow an injection procedure or allow a purging or priming sequence using the fluid control module.

Clause 14: The fluid injection system as recited in Clause 13, wherein the state logic protocol created by the fluid control module comprises: in the event the pressure wave information is indicative of fluid communication between the third fluid path set and the patient's vasculature, instructing the fluid control module to allow the injection procedure, while preventing the purging or priming sequence; and in the event the pressure wave information is indicative of no fluid communication between the third fluid path set and the patient's vasculature, instructing the fluid control module to allow the purging or priming sequence.

Clause 15: The fluid injection system as recited in Clause 13 or 14, wherein the pressure isolation valve comprises an automatic spring-biased spool valve.

Clause 16: The fluid injection system as recited in any of Clauses 13-15, further comprising a transducer positioned in-line with the second fluid path set, wherein the transducer is configured to monitor and convert a fluid flow pressure of the medical fluid within the second fluid path set into the electrical signals to be sent to the hemodynamic monitoring system.

Clause 17: The fluid injection system as recited in Clause 16, further comprising a hemodynamic monitoring mechanism positioned in-line between the transducer and the hemodynamic monitoring system.

Clause 18: The fluid injection system as recited in any of Clauses 13-17, further comprising an air detector positioned in-line with the third fluid path set.

Clause 19: A method of monitoring fluid pressure within a fluid injection system, the method comprising: directing a medical fluid through a fluid path set of the fluid injection system; measuring a fluid pressure of the medical fluid using a transducer positioned in-line with the fluid path set; sending fluid pressure information from the transducer to a hemodynamic monitoring system; converting the fluid pressure information into pressure wave form information using the hemodynamic monitoring system; sending the pressure wave form information to a fluid control module of the fluid injection system; and allowing an injection procedure or allowing a priming sequence and a purging sequence using the fluid control module based on the pressure wave form information.

Clause 20: The method as recited in Clause 19, further comprising displaying the pressure wave information on a graphical user interface of the fluid injection system.

These and other features and characteristics of the system, as well as the methods of operation and functions of the related elements of the system, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only, and are not intended as a definition of the limits of the disclosure. As used in the specification and claims, the singular form of "a", "an", and "the" include plural referents unless the context clearly dictates otherwise.

DESCRIPTION OF THE DISCLOSURE

For purposes of the description hereinafter, the terms "upper", "lower", "right", "left", "vertical", "horizontal", "top", "bottom", "lateral", "longitudinal", and derivatives thereof, shall relate to the disclosure as it is oriented in the figures. However, it is to be understood that the disclosure may assume alternative variations and step sequences, except where expressly specified to the contrary. It is also to be understood that the specific systems and processes illustrated in the attached drawings, and described in the following specification, are simply exemplary examples of the disclosure. Hence, specific dimensions and other physical characteristics related to the examples disclosed herein are not to be considered as limiting.

As used herein in the context of communication between two or more units or devices, the terms "communication" and "communicate" refer to the receipt, transmission, or transfer of one or more signals, messages, commands, or other types of data. For one unit or device to be in communication with another unit or device means that the one unit or device is able to receive data from and/or transmit data to the other unit or device. A communication may use a direct or indirect connection, and may be wired and/or wireless in nature. Additionally, two units or devices may be in communication with each other even though the data transmitted may be modified, encrypted, processed, routed, etc., between the first and second unit or device. It will be appreciated that numerous arrangements are possible. Any known electronic communication protocols and/or algorithms may be used such as, for example, UDP, TCP/IP (including HTTP and other protocols), WLAN (including 802.11 and other radio frequency-based protocols and methods), analog transmissions, cellular networks, and/or the like. As used herein to describe a fluid pathway, the term "fluid communication" refers to whether fluid may flow between two described portions of a device. For example, an injector may be in fluid communication with a patient's vasculature when fluid may flow from the injector to the patient's vasculature. Alternatively, an injector may not be in fluid communication with a patient's vasculature when the fluid pathway is blocked, for example, by closing a stopcock, and fluid may not flow from the injector to the patient's vasculature.

Figure 1:
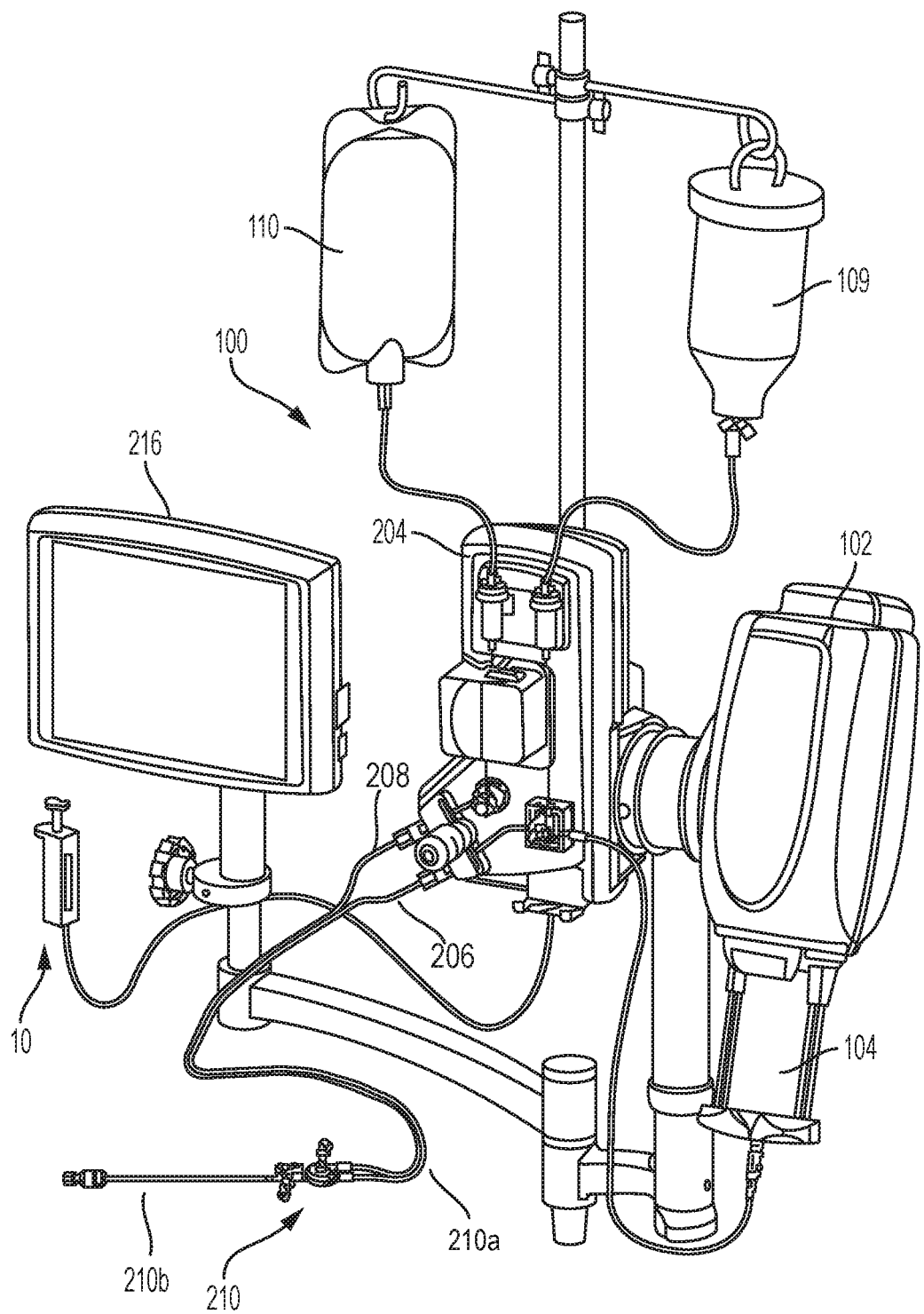
FIG. 1 is a perspective view of a fluid delivery system according to one example of the present disclosure.
Figure 2:
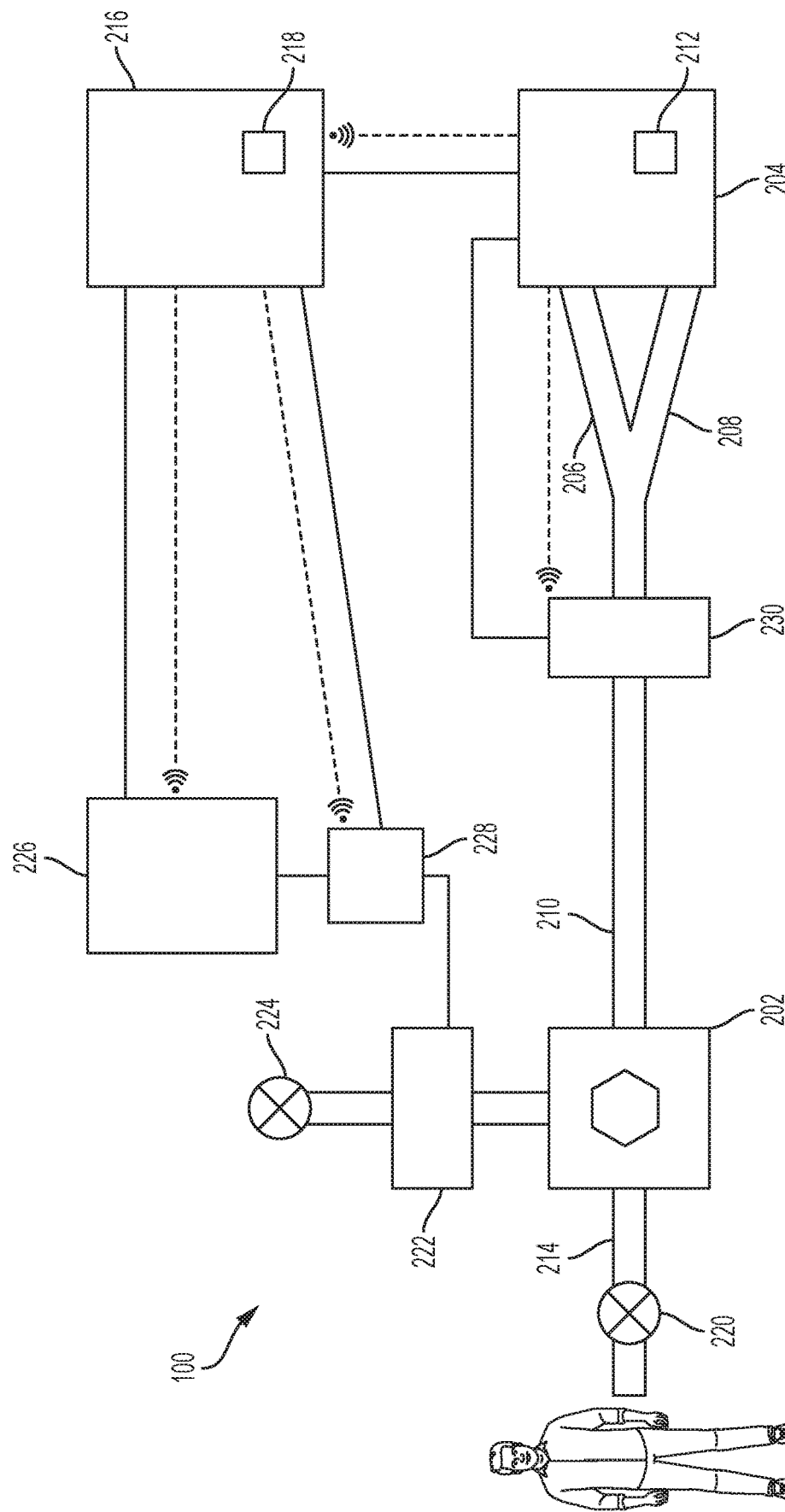
FIG. 2 is a schematic view of a fluid injector state logic system according to one example of the present disclosure.

As disclosed in FIGS. 1 and 2, in one example of the disclosure, a fluid delivery system 100 (also referred to as a fluid injection system) generally includes a powered injector 102 that is adapted to support and actuate a syringe 104 used to inject an injection fluid (also referred to as a medical fluid) to a patient during a medical procedure, such as an angiographic procedure. Examples of such a fluid delivery system are disclosed in U.S. Pat. No. 9,433,730, which is hereby incorporated by reference in its entirety and may also include injectors such as the Medrad® Avanta™ Injector and Medrad® Mark 7 Arterion® Injector available from Bayer HealthCare LLC. In typical angiographic procedures, the injection fluid is contrast media and such procedures further include saline as an additional or secondary injection fluid or flushing agent that is supplied to the patient.

In one example illustrated in FIGS. 1 and 2, a fluid injection system 100 may comprise a fluid injector 102 operatively associated with a fluid control module 204. The fluid control module 204 is generally adapted to fluidly connect a syringe 104 to a source of contrast media 109 and fluidly connect a source of saline 110 a fluid path set 206, 208, 210 and the fluid control module 204 is further adapted to support the fluid path set 206, 208, 210 and control fluid flow between the fluid path set 206, 208, 210 and the upstream components of the fluid injection system 100. The fluid path sets 206, 208 may converge to form a single dual-lumen fluid path set 210a which may further converge to a single-lumen fluid path 210b. The fluid path set 210 further connects the syringe 104 and source of saline 110 to a catheter that is associated with the patient for supplying the contrast media and saline to the patient. The contrast media flow from the syringe 104 and the saline flow to the patient is controlled by the fluid control module 204, which also controls the various valves and flow regulating structures in the fluid path set 206, 208, 210 to regulate the delivery of contrast media and saline to the patient based on the input commands provided by the physician or user. In one example, the physician controls the input commands to the fluid control module 204 using a hand controller 10. The hand controller 10 may be directly connected or wired to the fluid control module 204. In another example, the hand controller 10 may also be connected directly with the fluid injector 102. In a further example, the hand controller 10 may be wirelessly connected to at least one of the fluid injector 102 and the fluid control module 204. The fluid injector 102 and the fluid control module 204 are desirably in electronic data communication and the choice of associating the hand controller 10 with either the fluid injector 102 or the fluid control module 204 primarily depends on the computer hardware and software associated with the fluid injector 102 and/or the fluid control module 204. This computer hardware and software forms a control unit for the fluid injector 102 and/or fluid control module 204. The fluid control module 204 may be programmed to run different preprogrammed injector procedures, such as priming the fluid path set 206, 208, 210, injecting the medical fluid into the patient at specific flow rates and volumes, and purging the fluid path set 206, 208, 210 of any medical fluid before or after the injection procedure. In one example, the fluid control module 204 may include a monitoring control module 212 configured to receive data information from different components of the system, as will be described below. The monitoring control module 212 may be configured to receive data information either wirelessly (dotted line with wireless symbol) or directly (solid line) from different components in the system. The monitoring control module 212 may include one or more algorithms for evaluation of the signal or data information received from the different components of the system and decision making criteria for operating the system 100 based on the signal or data information received by the monitoring control module 212. In some examples, the fluid delivery system 100 may include a syringe-based fluid delivery system, a peristaltic pump-based delivery system, or combinations of both. It is also considered that the system 100 may be adapted for high pressure systems that are typical in angiographic and cath labs, typically in the range of 1200 psig.

The system 100 and fluid injector 102 are generally used to supply the contrast media under pressure to the fluid path set 206, 210 and, ultimately, the patient through a patient fluid path set 214. In one example, a rotating connection 220 or other fluid control mechanism may be included on a patient connection end of the fluid path set 214 to control flow of medical fluid therethrough. For example, the rotating connection valve 220 may be a three-way stopcock which has at least three positions: a first position that allows fluid communication between the fluid control module 204 and the patient; a second position that allows fluid communication between the fluid control module 204 and a waste port (not shown); and a third closed position where fluid communication between the fluid control module 204 and any component downstream of the valve 220 is blocked. In one example, the injector 102 may be controlled by the hand controller 10 to supply the contrast media at discrete and preselected flow rates based on the physical inputs of the hand controller 10. In another example, a user interface display, such as a graphical user interface ("GUI") 216 and/or data entry device, may be provided for a user to manually input control parameters for operation of the fluid injector 102 and/or the fluid control module 204. The graphical user interface 216 may include a monitoring control module 218 configured to receive data information from different components of the system, as will be described herein. The monitoring control module 218 may be configured to receive data information either wirelessly or directly from one or more different components in the system, such as, for example, the fluid control module 204, the monitoring control module 212 of the fluid control module 204, a hemodynamic monitoring system 226, and/or a hemodynamic monitoring mechanism or jump box 228. The monitoring control module 218 may include at least one algorithm for evaluation of the signal or data information received from the one or more different components of the system and include decision making criteria for operating the system 100 based on the signal or data information received by the monitoring control module 218. In a further example, input control parameters could be remotely sent to the injector 102 and/or the fluid control module 204, for example by the user through the GUI 216 and corresponding data entry device.

Referring to FIG. 2, in various embodiments the fluid injection system 100 may include a pressure isolation valve 202, such as an automatic pressure isolation valve. As used herein, an "automatic pressure isolation valve" refers to a pressure isolation valve that operates in the absence of user input, for example in response to fluid pressure, fluid flow, etc. In one example, the pressure isolation valve 202 may be a flow-based or spring-based spool valve. In other examples, the pressure isolation valve 202 may be a high pressure crack valve or an electro-mechanical pressure isolation valve. In various aspects, the pressure isolation valve 202 closes when flow of contrast media, saline, or medical fluid occurs. Non-limiting examples of a flow-based pressure isolation valves are disclosed in U.S. Pat. Nos. 7,094,216; 7,610,936; 8,540,698; and 9,895,527, the disclosures of which are incorporated herein in their entirety. Therefore, when the pressure isolation valve 202 is in the closed position, fluid pressure is blocked from reaching a transducer 222, thereby preventing damage to the transducer 222. The pressure isolation valve 202 may be reconfigured to adjust the required amount of pressure from the contrast media necessary to compress the spring to close the passage through the pressure isolation valve 202 thereby preventing fluid communication between the contrast fluid line 210 and the transducer 222. A stopcock 220 may be positioned in-line with the fluid path set 214 to the patient. The stopcock 220 may be rotatable between an open position that permits medical fluid to pass through the fluid path set 214; a waste position that blocks the medical fluid from passing therethrough to the patient and being directed out of a waste port to direct fluid out of the fluid path set 214 during a purging or priming sequence; and a fully closed position where flow from the fluid path set 214 through the stopcock 220 is blocked.

In various embodiments, a transducer 222 may be provided in fluid communication with the pressure isolation valve 202 and may be configured to monitor and convert the fluid flow pressure of the medical fluid within the fluid path set 206, 208, 210 and/or the fluid path set 214 into electrical signals sent to a hemodynamic monitoring system 226 in communication with the transducer 222. When the fluid path set 214 in fluid communication with the patient, the medical fluid flows to the patient's arterial vasculature during an injection procedure. When the patient is fluidly connected with fluid path set 214, i.e., fluid path set 214 is primed with a medical fluid, the patient's heart pumps blood through the vascular system and a fluid pressure fluctuation is created by the variations in the blood pressure due to the heart beat may be measured within the fluid path set 214 based on the beating of the patient's heart. Thus, when a fluid path between the patient and the transducer 222 is in fluid communication, as the patient's heart pumps, the fluctuation of fluid pressure generated within the patient's vasculature is translated through the medical fluid in the fluid path set 214 to transducer 222 and may be converted to an electrical signal by transducer 222. As the fluid flow pressure is monitored by the transducer 222, hemodynamic pressure of the patient may be monitored by the hemodynamic monitoring system 226. Specifically, the fluid flow pressure values read by the transducer 222 may be converted to electrical signals that are sent to the hemodynamic monitoring system 226 to allow the system 100 and/or medical professional to monitor the patient's hemodynamic pressure. Further, a measurement of a patient's hemodynamic pressure by the system is an indication that the patient is in fluid communication with the fluid injection system 100, i.e., that any fluid flow from the system will be transferred to the patient's vasculature system.

Figure 3A:
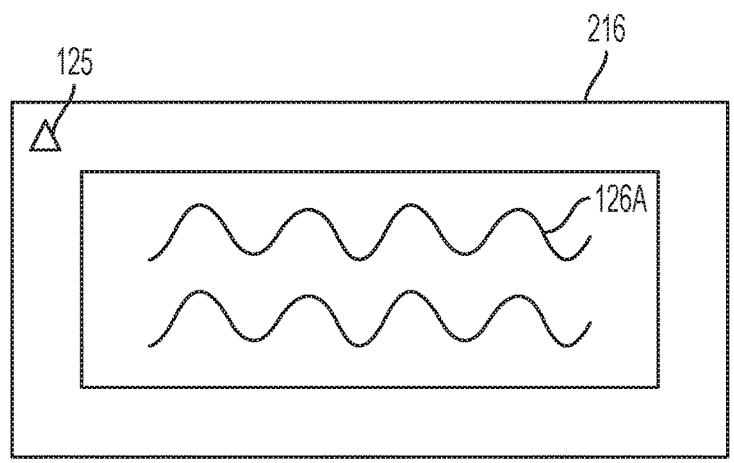
FIG. 3A is an illustration of a pressure wave form generated by a hemodynamic monitoring system according to one example of the present disclosure.

In one example, the hemodynamic monitoring system 226 is a system configured to measure the pressure and/or flow of blood within the patient's cardiovascular system and pressure and/or flow of medical fluid within the fluid path sets 206, 208, 210, 214 using the transducer 222. In various embodiments, transducer 222 may be a pressure transducer. Hemodynamic monitoring of the patient is the measurement and interpretation of biological systems within the patient that describes the performance of the patient's cardiovascular system. The hemodynamic monitoring system 226 may be in electrical communication with the transducer 222. The electrical signals generated by the transducer 222, which are correlative to the blood pressure within the patient and fluid flow pressure within the fluid path set 214, are sent to the hemodynamic monitoring system 226, which may generate pressure wave forms 126A, as shown in FIG. 3A, based on the electrical signals received from transducer 222. Pressure wave forms 126A correspond to pressure fluctuations within a patient's vasculature, for example, due to systolic and diastolic blood pressure values.

When the pressure isolation valve 202 is and the transducer 222 are in fluid communication with the patient's vasculature system, the patient's heart will beat causing fluid flow pressure within the fluid path sets 206, 208, 210, 214, which is monitored and converted into electrical signals by the transducer 222. The electrical signal corresponding to the fluid flow pressure created by the pumping of the patient's heart is sent to the hemodynamic monitoring system 226. As shown in FIG. 3A, when the fluid lines are fully primed (i.e., no significant air) and the patient's vasculature is in fluid communication with the transducer 222, based on the fluid flow pressure generated by the patient's heart, the hemodynamic monitoring system 226 generates a first pressure wave form 126A that may be displayed on a graphical interface unit (not shown) of the hemodynamic monitoring system 226 and/or on the graphical user interface 216 of the injector system 100 (see FIG. 2). The pressure wave forms 126A that are generated are indicative of the amount of fluid flow pressure that is being generated in the fluid path set 214, which indicates that valve 220 and the pressure isolation valve 202 are in the open position allowing fluid communication between the patient and the fluid path set 210. By monitoring the pressure wave forms 126A, the physician is provided real-time monitoring of the patient's heart functionality and also allows the physician to determine if the patient is fluidly connected to injection system 100.

Based on the pressure wave forms 126A that are generated, the physician may be able to determine whether the fluid path set 214 is properly positioned in the heart and/or vasculature of the patient. Different positions in the patient's heart and vasculature will generate different pressure wave forms such that the physician can interpret the specific pressure wave form to determine the location of the catheter in the patient's vasculature. When the valve 220 is open to the patient, the fluid path set 210 and/or fluid path 214 should not be purged or primed since unwanted air present in the fluid path could be directed into the patient's vasculature. To purge the system, the valve 220 may be moved to the closed position/waste port position. Thereafter, the fluid control module 204 may push fluid through the fluid path sets 206, 208, 210 to prime/purge any air present in the fluid path sets 206, 208, 210, 214 out through the waste port 220. It is possible to purge both fluid path sets 210, 214 when a patient is not connected to the fluid injection system 100 by opening the valve 220 to discharge any air trapped in the fluid path sets 210, 214 from a distal end of the fluid path set 214, for example at the connector at the end of fluid path set 214 for connecting the fluid injection system 100 to the patient. This type of purging should only be conducted when the generated pressure wave forms indicate that the fluid path set 214 is no longer connected to the patient. According to various embodiments, it is possible to determine when a patient is not connected to the fluid injection system 100. By reviewing the hemodynamic monitoring system 226, either by manual or electronic means, before initiating the priming or purging process, the physician may be alerted to the current position of valve 220. In various embodiments, the physician and/or a state logic protocol of the monitoring control module 212 can ensure that the fluid path set 214 is not in fluid communication with the patient before initiating a purging or priming process by reviewing the pressure wave form information from the hemodynamic monitoring system 226, thereby preventing air from being delivered to the patient's vasculature. In certain embodiments, to further assist the physician, the fluid control module 204, and/or the monitoring control module 212 in determining whether air is present in the fluid path set 214, an air detector 230 may be positioned in-line with the fluid path set 210. The air detector 230 may be configured to send signals to the fluid control module 204 to alert the physician when air has been detected in the fluid path set 210, thereby indicating that the fluid path set 210 should be purged or primed. The air detector 230 may be in direct or wireless communication with the fluid control module 204 to send data information regarding the presence and/or amount of air in the fluid path set 210. In the event the air detector 230 detects air in the fluid path set 210, the air detector 230 may send an alert notification to the fluid control module 204 regarding the air detected in the fluid path set 210. Based on this alert notification, the fluid control module 204 may be configured to cease any injection procedure that is currently being completed so as to prevent the air in the fluid path set 210 from being injected into the patient and also notify the user of the air detection event so that the user may take the appropriate action to remove the air and avoid injection of the air into the patient. Once the alert notification is no longer sent form the air detector 230, the fluid control module 204 will identify that no air exists in the fluid path set 210 and an injection procedure can be re-initiated. In one example, the air detector 230 is inoperative during a purging or priming sequence.

Figure 3B:
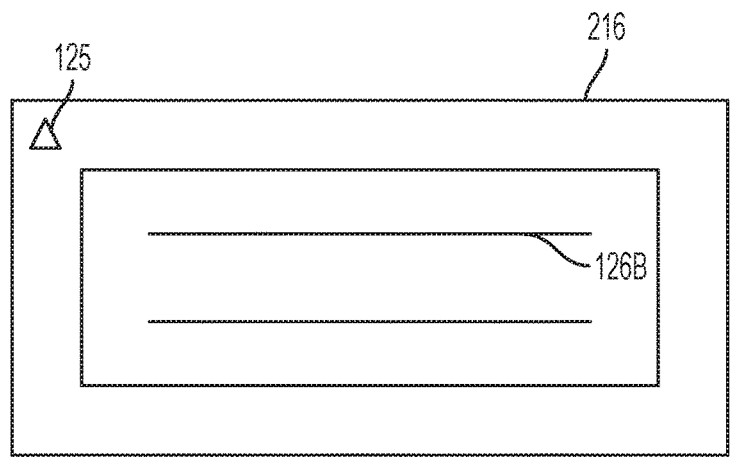
FIG. 3B is an illustration of another pressure wave form generated by a hemodynamic monitoring system according to one example of the present disclosure.

When the valve 220 is closed, fluid communication between the injector and the patient is broken. The patient's heart beat will continue but the fluid pressure generated by the patient's heart cannot be detected by the transducer 222 since the valve 220 has prevented fluid communication between the patient's vasculature and the transducer 222. Due to the lack of blood pressure fluctuations being detected by the transducer, the resulting electronic signals sent to the hemodynamic monitoring system 226 will produce a second pressure wave form 126B generated by the hemodynamic monitoring system 226 having a zero or low (e.g., fluctuations due to system noise or other phenomena unrelated to a patient's heart beat) value, as shown in FIG. 3B. The pressure wave forms 126B that are generated are indicative of the lack of fluctuation of fluid pressure in the fluid path set 214 as generally observed in connection with heart beat pressure variations, which indicates that the valve 220 is in the closed to the patient position and/or that the patient is no longer fluidly connected to fluid path set 214. Since the valve 220 is closed to the patient and moved to a position providing fluid communication with a waste container (for example a 3-way valve with a first connection to fluid path 214, a second connection to the patient, and a third connection to a waste container), the fluid path sets 206, 208, 210, 214 can be purged or primed to remove any air from the fluid path sets, and unwanted air would be directed to the waste container and not be directed into the patient's vasculature. In other embodiments, any air can be removed from the fluid path sets 206, 208, 210 upstream of the closed valve 220 and the patient's vasculature via a waste port included on a stopcock 224 that is in fluid communication with the transducer 222 and the pressure isolation valve 202. The stopcock 224 may be moved between an open position and a closed position. The stopcock 224 may be positioned in the closed position to prevent fluid from being directed out of the system 100. The stopcock 224 may be positioned in the open position to permit fluid to be directed out of the system 100 during a purging or priming sequence.

As shown in FIG. 2, the hemodynamic monitoring system 226 may be in communication with the graphical user interface 216. As used herein with regard to electrical signals between components of the system 100, the terms "communication" and "communicate" refer to the receipt, transmission, or transfer of one or more signals, messages, commands, or other type of data, which may be either in digital and/or analog format. For one unit or device to be in communication with another unit or device means that the one unit or device is able to receive data from and/or transmit data to the other unit or device. A communication may use a direct or indirect connection, as shown in FIG. 2 by the solid lines and dashed lines respectively, and may be wired and/or wireless in nature. Additionally, two units or devices may be in communication with each other even though the data transmitted may be modified, encrypted, processed, routed, etc., between the first and second unit or device. It will be appreciated that numerous arrangements are possible and that electrical communication may potentially proceed through one or more intervening devices. Any known electronic communication protocols and/or algorithms may be used such as, for example, UDP, TCP/IP (including HTTP and other protocols), WLAN (including 802.11 and other radio frequency-based protocols and methods), analog transmissions, cellular networks, WiFi, Bluetooth, and/or the like.

In one example, the hemodynamic monitoring system 226 may be configured to send the pressure wave form information received from the transducer 222 to at least one of a first monitoring control module 218 of the graphical user interface 216 and a second monitoring control module 212 of the fluid control module 204. Based on the information received from the hemodynamic monitoring system 226 and/or the transducer 222, the monitoring control module 212 of the fluid control module 204 and/or the monitoring control module 218 of the graphical user interface 216 may be configured to create a state logic protocol, in both a binary form and a quantitative algorithm to determine different states of the system 100, such as, for example, fluid path sets 206, 208, 210, 214. According to various embodiments, based on the state of the fluid path sets 206, 208, 210, 214 as determined by the hemodynamic monitoring system 226 and shown on the graphical user interface 216, the monitoring control module 218 of the graphical user interface 216 may send commands to the monitoring control module 212 of the fluid control module 204 to perform certain procedures and protocols, such as allowing or not allowing specific procedures or protocols based on injector state information. In one example, in the event the pressure wave form information sent to the monitoring control module 218 of the graphical user interface 216 indicates the valve 220 is opened based on the pressure wave pulses detected by the transducer 222, for example as shown in FIG. 3A, the monitoring control module 218 of the graphical user interface 216 may send command instructions to the monitoring control module 212 of the fluid control module 204 instructing the fluid control module 204 to allow an injection procedure to deliver medical fluid to the patient, while preventing the fluid control module 204 from initiating a priming or purging procedure that could send unwanted air into the patient's vasculature. It is contemplated that the monitoring control modules 212, 218 may provide options to the physician to set limits for the pressure wave forms to notify the fluid control module 204 when an injection procedure is authorized. These limits may be manually set by the physician based on the specific condition of the patient, for example determined from the average values for blood pressure of the patient, or minimum values for blood pressure of the patient, as measured by a transducer system similar to the present disclosure. It is also contemplated that the physician may select the limits from a selection of actual patient pressure wave forms that are pre-recorded on the monitoring control module 212, 218 or are read in real-time from the transducer 222. In one example, after the fluid path set 214 has established fluid communication with the patient, the physician may record the fluid pressure detected by the transducer 222 of the patient in the initial state and set this fluid pressure as a baseline for the patient. The physician may then establish upper and lower fluid flow pressure limits for the pressure wave forms that will determine whether the fluid control module 204 is permitted to initiate an injection procedure. In certain embodiments, the monitoring control modules 212, 218 may also have the ability to record and build a library of pressure wave form history for the patient, so that the physician can monitor and analyze the fluid flow pressure and adjust the pressure wave limits if needed. According to various embodiments, the injector state logic may then utilize one or more of these measured pressure wave forms to determine a protocol for one or more patients.

Figure 3C:
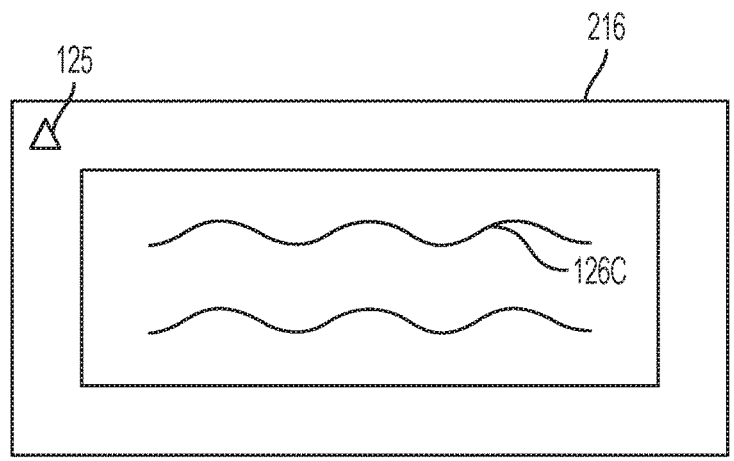
FIG. 3C is an illustration of another pressure wave form generated by a hemodynamic monitoring system according to one example of the present disclosure.

The monitoring control module 218 of the graphical user interface 216 may include an alert feature that allows the graphical user interface 216 to indicate to the physician that valve 220 is open to the patient and the fluid injection system 100 is in fluid communication with the patient's vasculature and that a priming or purging procedure of the injector should not be initiated or allowed. In one example, the alert feature may be a warning light or audible alert displayed on or generated by the graphical user interface 216, or a tactile sensation in the hand controller 10 indicating that a prime/purge procedure should not be initiated. In certain embodiments, the alert may disable the initiation of a priming or purging procedure until the user has reviewed the system configuration and acknowledged that the event that caused the alert has been addressed. In various examples, as shown in FIGS. 3A-3C, the graphical user interface 216 may display a visual indicator 125 and/or provide an audible alert to the physician regarding the status of the system 100 based at least in part by the pressure wave forms detected by the hemodynamic monitoring system 226. The visual indicator 125 and/or audible alert may be a warning indicator that informs the physician when the measured fluid flow pressure is outside of a possible human intra-coronary pressure range. In the event a warning indicator is issued by the graphical user interface 216, an indication is presented to the physician to indicate that air may be present in at least one of the fluid path sets 206, 208, 210, 214 and that the event that caused the alert must be addressed. In another embodiment, the visual indicator 125 and/or audible alert may be a caution indicator that informs the user when the measured fluid flow pressure is outside of a normal human intra-coronary pressure range, but within the possible human intra-coronary pressure range. In this embodiment, the physician or user may be required to review the event and acknowledge that the issue has been reviewed before continuing. In another embodiment, the visual indicator 125 and/or audible alert may be a ready-to-use indicator that indicates that the measured fluid pressure is within the normal human intra-coronary pressure range, or within the predetermined pressure range as determined on a patient-by-patient process. Non-limiting examples of this visual indicator 125 are disclosed in U.S. Pat. No. 9,486,579, which is hereby incorporated by reference. In another aspect, the graphical user interface 216 may send one or more commands to the hand controller 10 to shut down the operation of the hand controller 10, thereby preventing the injection procedure from proceeding. The alert or disabling of the injector 102 and/or hand controller 10 may be effective until fluid connection between the injector fluid paths 206, 208, 210, 214 and the patient is shut off, for example by closing valve 220 to the patient and optionally providing fluid communication between the injector fluid paths 206, 208, 210, 214 and a waste container and subsequently performing a priming or purging procedure to remove air from injector fluid paths 206, 208, 210, 214.

In another embodiment, in the event that the pressure wave form information sent to the monitoring control module 218 of the graphical user interface 216 indicates the valve 220 is closed based on due to zero or low (due to system noise) pressure wave forms from the hemodynamic monitoring system 226 through patient fluid path set 214, as shown in FIG. 3B, as detected by the transducer 222, the graphical user interface 216 and/or monitoring control module 218 may send instructions to the monitoring control module 212 of the fluid control module 204 instructing the fluid control module 204 to allow a purge or priming procedure in the fluid path sets 206, 208, 210, 214 to remove any entrapped air from the fluid path sets. In certain embodiments, the graphical user interface 216 may generate an alert condition to the physician indicating that the fluid control module 204 can be used to prime or purge the fluid path sets 206, 208, 210, 214. This alert condition may be a visual indicator or audible alert generated by the graphical user interface 216, or a tactile sensation in the hand controller 10. In this example, since the hemodynamic monitoring system 226 has indicated that fluid communication between the patient and the fluid control module 204 is blocked by the valve 220 and/or that the fluid path set 214 is no longer in fluid communication with the patient's vasculature, the fluid path sets 206, 208, 210, 214 may be primed or purged by forcing medical fluid, such a saline or a contrast, through the fluid path sets 206, 208, 210, 214 to push out any extra medical fluid and entrapped air in the fluid path sets 206, 208, 210, 214. According to certain embodiments, the medical fluid may be primed into a waste container in fluid connection through valve 220 and/or valve 224.

In other embodiments of the present disclosure, the graphical user interface 216 may control the fluid control module 204 such that, before the fluid control module 204 can initiate an injection procedure, the graphical user interface 216 must first determine that the fluid path sets 206, 208, 210, 214 have been fully purged/primed so that no unwanted air remains in the fluid path sets 206, 208, 210, 214. For example in certain scenarios, the fluid path sets 206, 208, 210, 214 may have gone through a prime/purge cycle but some air remains in the fluid path sets. According to these embodiments, the system 100 and injector state logic may be configured to detect the remaining air in the system and require the physician to repeat the purge/prime process to remove the detected air. Whether air remains in the fluid lines after a purge/prime cycle may be detected by the shape of the pressure wave form from the hemodynamic monitoring system 226. For example, in the event any air remains in the fluid path set 206, 208, 210, 214, the pressure wave forms 126C generated by the hemodynamic monitoring system 226 may not be as large or strong as when fluid pressure is measured when no air is present in the fluid path sets 206, 208, 210, 214, but may be greater than when the system is substantially filled with air prior to a priming procedure and zero or low fluid pressure fluctuation detected in the fluid path sets 206, 208, 210, 214. This may be due to any pressure signal read by the transducer 222 being muted by the presence of amounts of air in the fluid path sets. According to these embodiments, the muting of the pressure signal may be due to the increased compressibility of air, relative to the liquid in the line. As shown in FIG. 3C, the pressure wave forms 126C may be slightly "fuzzy" or minimal, falling somewhere between a full fluid filled line and an air filled line and indicating that there may be unwanted air or medical fluid in at least one of the fluid path sets 206, 208, 210, 214. In various embodiments, the pressure wave forms 126C may be smaller in intensity than the pressure wave forms 126A but greater than pressure wave forms 126B. If the graphical user interface 216 detects that a small amount of air or medical fluid remains in the fluid path sets 206, 208, 210, 214, as determined by detection of a pressure wave form similar to 126C, the graphical user interface 216 may lock the system 100, such as the fluid control module 204, from allowing an injection procedure until the fluid path sets 206, 208, 210, 214 are completely purged or primed of air as the situation may dictate. After the purging/priming procedure has been conducted, the graphical user interface 216 again evaluates the pressure wave forms 126 that are generated by the hemodynamic monitoring system 226 to determine whether the fluid path sets 206, 208, 210, 214 have been completely purged of unwanted air and if the pressure wave form still is similar to pressure wave form 126C, the system may require further priming or user intervention before allowing an injection procedure to proceed. For example, if the event the pressure wave forms 126C continue to be a little fuzzy, the graphical user interface 216 keeps the system 100 locked and the fluid control module 204 and/or the physician will be instructed to re-initiate the purging/priming procedure again with appropriate automated or physician control of valve 220 to prevent air injection into the patient during the purging/priming. This process repeats until the graphical user interface 216 determines, for example based on the injector state logic protocol, that all of the air has been purged from the fluid path sets 206, 208, 210, 214 and an appropriate pressure wave 126A is observed. At this point, the graphical user interface 216 may instructs the fluid control module 204 to allow the injection procedure to proceed. In other embodiments, the injection procedure can be re-initiated by the physician or automatically by the monitoring control module 212 of the fluid control module 204.

In another example of the present disclosure, a hemodynamic monitoring mechanism or jump box 228 may be provided on an electrical line connecting the transducer 222 to the hemodynamic monitoring system 226. As used herein, the term "jump box" means an electronic device that may be inserted in-line for direct connection or wirelessly connected between the transducer and the hemodynamic monitoring system which is capable of receive and duplicate electrical signals from the transducer and sends them to the graphical user interface, and optionally the corresponding monitoring control module, for analysis, monitoring, and/or display to the physician. In one embodiment, in the event the hemodynamic monitoring system 226 cannot be connected in effective communication with the graphical user interface 216, the hemodynamic monitoring mechanism or jump box 228 may be used to intercept the signal from the pressure transducer 222 and send pressure wave form information regarding the fluid pressure in the fluid path sets 206, 208, 210, 214 to the graphical user interface 216. In certain embodiments, the hemodynamic monitoring mechanism or jump box 216 may wrap around the electrical line connecting the transducer 222 or be inserted into the electrical line and the hemodynamic monitoring system 226 to monitor and record the fluid pressure information. In other embodiments similar to the hemodynamic monitoring system 226, the hemodynamic monitoring mechanism or jump box 228 may be configured to convert the fluid pressure information from the transducer 222 into pressure wave forms 126A, B, or C and transmit them to the graphical user interface 216. The pressure wave form information may be sent to the graphical user interface 216 to generate the static logic protocol described herein. The hemodynamic monitoring mechanism or jump box 228 and the graphical user interface 216 may be in direct or wireless communication with one another.

Figure 4:
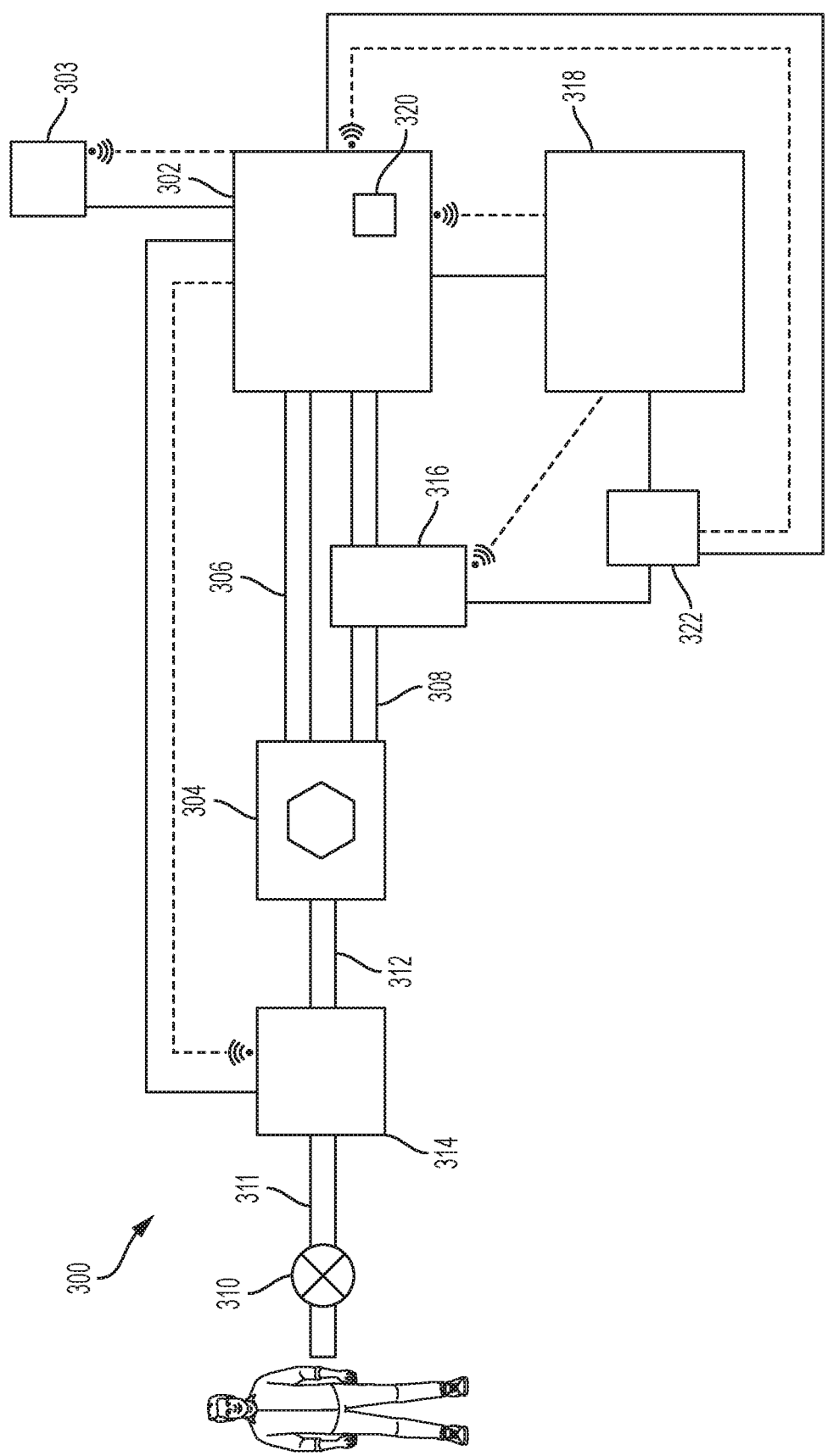
FIG. 4 is a schematic view of a fluid injector state logic system according to one example of the present disclosure.

With reference to FIG. 4, a fluid delivery system 300 according to an embodiment of the present disclosure is shown and described in detail. The system 300 may include a fluid control module 302 in fluid communication with a pressure isolation valve 304 via at least two separate fluid path sets 306, 308, and a graphical user interface 303. The graphical user interface 303 may include a monitoring control module (not shown) to receive data and information from other components of the system 300. The graphical user interface 303 operates in a similar manner as the graphical user interface 216 described above in connection with the system 100. The fluid path sets 306, 308 may be connected to the fluid control module 302 and may be configured to deliver contrast media and saline, respectively, to a patient. In certain embodiments, the contrast media and saline may be supplied from fluid sources fluidly connected to the fluid control module 302. An additional fluid path set 311 and 312 may be fluidly connected to an air detector 314 at one end thereof and a patient's vasculature at an opposing end of fluid path set 311. The air detector may be in fluid communication with the fluid path sets 311 and 312, or in other embodiments may clamp over or around one or both of fluid path sets 311 and 312. In various embodiments, one or more rotating connection 310, such as a two or three-way stopcock, may be included on a patient connection end of the fluid path set 311 to control flow of medical fluid therethrough to the patient or a waste container. An additional fluid path set 312 may extend between the pressure isolation valve 304 and the air detector 314.

In various embodiments, the pressure isolation valves 202 and 304 may be an automatic pressure isolation valve, such as a spring-loaded spool valve, a flow-based valve, or a pressure-based valve. In other embodiments, the pressure isolation valve 202/304 may be a high pressure crack valve. In this example, the pressure isolation valve 202/304 includes a spring-loaded spool that is normally in an open position to permit the fluid communication through the pressure isolation valve from the patient to the pressure transducer 222/316 to allow reading of the pressure wave form due to the patient's heart beat, while preventing high pressures of the contrast media to pass through the pressure isolation valve 202/304 to the pressure transducer 222/316. In the event the fluid control module 302 is instructed to direct contrast media to the patient, the contrast media may be pushed through the pressure isolation valve 304 by the fluid control module 302 into the patient's vasculature. According to certain embodiments, the pressure of the contrast media in the pressure isolation valve 304, for example against the spool of the pressure isolation valve 304 causes the spool to compress the spring therein and block the passage of the saline through the pressure isolation valve 304 to permit the contrast media to be directed to the patient. In one example, when the pressure isolation valve 304 is in the position where there is fluid communication between the contrast line 306, pressure is blocked from reaching the transducer 316 to prevent damage to the transducer 316 due to exposure to the high pressures typically used in contrast injections in angiographic procedures. The pressure isolation valve 304 may be reconfigured to adjust the required amount of pressure from the contrast media necessary to compress the spring to close the saline passage through the pressure isolation valve 304.

A valve 310, such as a stopcock, may be positioned in-line with the fluid path set 311 that extends from the pressure isolation valve 304 to the patient. The stopcock 310 may be rotatable between an open position that permits medical fluid to pass through the fluid path set 312 to the patient and a waste position that blocks the medical fluid from passing therethrough to the patient and instead directs the fluid out of a waste port to direct fluid out of the fluid path set 312 during a purging or priming sequence. An air detector 314 may also be provided in-line between the pressure isolation valve 304 and the patient. The air detector 314 may be configured to detect when any air that is present in the fluid path set 312 or the medical fluid therein. The air detector 314 may be in direct or wireless communication with the fluid control module 302 to send data information regarding the amount of air in the fluid path set 312. In the event the air detector 314 detects air in the fluid path set 312, the air detector 314 may send an alert notification to the fluid control module 302 regarding the air detected in the fluid path set 312. Based on this alert notification, the fluid control module 302 may be configured to alert a physician regarding the detection of air and/or cease any injection procedure that is currently being completed so as to prevent the air in the fluid path set 312 from being injected into the patient. The physician or the fluid injection system may then run a prime/purge cycle to remove the air from the fluid path 312 or system by rotating valve 310 to the waste position and purging/priming the system, before rechecking for the presence of air in the system or fluid pathways. Once air is no longer detected and the alert notification is no longer sent from the air detector 314, the fluid control module 302 will identify that no air exists in the fluid path set 312 and an injection procedure can be allowed to proceed. In one example, the air detector 314 may be inoperative during a purging or priming sequence initiated by the fluid control module 302.

With continued reference to FIG. 4, in various embodiments, a transducer 316 may be positioned in-line with the fluid path set 308 through which the saline is directed from the fluid control module 302 to the pressure isolation valve 304 and ultimately to the patient's vasculature system. The transducer 316 may be in direct or wireless communication with a hemodynamic monitoring system 318, such as described herein. In one embodiment, the transducer 316 may be a pressure transducer. The transducer 316 may be configured to monitor and convert the fluid flow pressure of the medical fluid within the fluid path set 308 into electrical signals which may be sent to the hemodynamic monitoring system 318 in communication with the transducer 316. When the fluid path set 308 is in fluid communication with the patient, the medical fluid flows to the patient's arterial vasculature during an injection procedure and fluid communication may be established between the transducer 316 and the patient's vasculature. As described herein, when the patient is fluidly connected with fluid path set 308 and transducer 316, i.e., valve 310 is in the open position and fluid path set 308 is completely primed with a medical fluid, the patient's heart pumps blood through the vascular system and a fluid pressure fluctuation is created within the fluid path set 308 based on the beating of the patient's heart. Thus, when a fluid communication between the patient and the transducer 316, by way of open valve 310, is established, as the patient's heart pumps, the fluctuation of fluid pressure generated within the patient's vasculature may be translated through the medical fluid in the fluid path set 308 to the transducer 316 and may be converted into electrical signals by the transducer 316. As the fluid pressure is monitored and converted to electrical signals by the transducer 316, a hemodynamic pressure of the patient may be monitored by the hemodynamic monitoring system 318. Specifically, the fluid pressure values generated by the transducer 316 may be converted to electrical signals that are sent to the hemodynamic monitoring system 318 to allow the system and/or medical professional to monitor the patient's hemodynamic pressure and the physician or system may create a state logic protocol regarding whether there is air in the system by the size/shape of the pressure wave form (126A, 126B, or 126C), as described herein, and determine whether to allow or prevent the injection to proceed or require a priming/purging sequence due the potential detection of air. The transducer 316 may operate similar to transducer 222 described above in connection with the fluid delivery system 100.

In one embodiment, the hemodynamic monitoring system 318 may be configured to send the pressure wave form information received from the transducer 316 to a monitoring control module 320 of the fluid control module 302 and/or the monitoring control module of the graphical user interface 303. Based on the information received from the hemodynamic monitoring system 318 and/or the transducer 316, the monitoring control module 320 of the fluid control module 302 may be configured to create a state logic protocol, in a binary form and/or a quantitative algorithm for the different states of the fluid path sets 306, 308, 311, 312. Based on the state of the fluid path sets 306, 308, 311, 312 as determined by the hemodynamic monitoring system 318, the monitoring control module 320 of the fluid control module 302 may be configured to perform certain procedures. In one embodiment, in the event the pressure wave form information sent to the monitoring control module 320 of the fluid control module 302 indicates the stopcock 310 is open and fluid path sets 306, 308, 311, 312 are fully primed based on the pressure wave pulses read by the transducer 316, the monitoring control module 320 of the fluid control module 302 may instruct the fluid control module 302 to allow the injection procedure and deliver medical fluid to the patient, while the fluid control module 302 is prevented from allowing a priming or purging procedure that could send unwanted air into the patient's vasculature. It is contemplated that the monitoring control module 320 may provide options to a physician to set limits for the pressure wave forms to notify the fluid control module 302 when an injection procedure is authorized, as described herein. These limits may be set manually by the physician based on the specific condition of the patient. It is also contemplated that the physician may select the limits from a selection of actual patient wave forms that are pre-recorded on the monitoring control module 320 or are read in real-time from the transducer 316. In one embodiment, after the fluid path set 308 has established fluid communication with the patient, the physician may read the fluid pressure measured from the transducer 316 and set this fluid pressure as a baseline for the patient. The physician may then establish upper and lower fluid pressure limits for the pressure wave forms that will determine whether the fluid control module 302 is permitted to initiate an injection procedure. The monitoring control module 320 may also have the ability to record and build a library of pressure wave form history for the patient, so that the physician can monitor and analyze the fluid pressure and adjust the pressure wave limits as needed. In the event the hemodynamic monitoring system 318 sends pressure wave information to the fluid control module 302 indicating that there are zero or low fluctuations in the fluid flow pressure, the fluid control module 302 may recognize that the stopcock 310 has been closed and/or open to the waste port so that fluid communication exists between the injector and the waste port so that the fluid path set 312 is no longer in fluid communication with the patient's vasculature or that the fluid path set 312 has been disconnected from the patient's vasculature. Therefore, in this condition, the fluid control module 302 is permitted to allow a purging or priming sequence through the fluid path sets 306, 308, 311, and 312. Therefore, the transducer 316, the hemodynamic monitoring system 318, the graphical user interface 303, and the monitoring control module 320 of the fluid control module 302 may operate in a similar manner as the transducer 222, the hemodynamic monitoring system 226, the graphical user interface 216, and the monitoring control module 212 of the fluid control module 204 described above in connection with the fluid delivery system 100 (FIG. 2).

The fluid delivery system 300 may also include a hemodynamic monitoring mechanism or jump box 322 provided in-line between the transducer 316 and the hemodynamic monitoring system 318 or attached to the communication line therebetween or otherwise in communication with at least one of the transducer 316 and the hemodynamic monitoring system 318. The hemodynamic monitoring mechanism or jump box 322 may be in direct or wireless communication with the fluid control module 302. The hemodynamic monitoring mechanism or jump box 322 may operate in a similar manner as the hemodynamic monitoring mechanism or jump box 228 described herein with reference to FIG. 2. Using the transducer 316, the hemodynamic monitoring system 318, and/or the hemodynamic monitoring mechanism or jump box 322, the system 300 may be configured to monitor pressure wave form information for the medical fluid directed through the fluid path sets 306, 308, 312 in a similar manner as described above in connection with the system 100 (FIG. 2).

While various examples of the system and methods of operating the system were provided in the foregoing description, those skilled in the art may make modifications and alterations to these examples without departing from the scope and spirit of the disclosure. For example, it is to be understood that this disclosure contemplates that, to the extent possible, one or more features of any example may be combined with one or more features of any other example. Accordingly, the foregoing description is intended to be illustrative rather than restrictive.

What is claimed is:

1. A fluid injection system, comprising:
 a graphical user interface;
 a fluid control module operatively connected to the graphical user interface;
 at least one monitoring control module operatively connected to at least one of the graphical user interface and the fluid control module;
 a fluid injector operatively connected to the graphical user interface and the fluid control module;
 at least one fluid path set in fluid communication with the fluid control module; and
 a hemodynamic monitoring system operatively connected to the at least one fluid path set and the monitoring control module,
 wherein the hemodynamic monitoring system is configured to receive electrical signals indicative of pressure waves formed in a medical fluid injected through the at least one fluid path set using the fluid injector based on a location of the at least one fluid path set in a patient's vasculature, to convert the electrical signals into pressure wave form information, and to send the pressure wave form information to the monitoring control module, and
 wherein based on the pressure wave form information received from the hemodynamic monitoring system, the monitoring control module is configured to create a state logic protocol to control the fluid control module to allow an injection procedure or allow a purging or priming sequence based on the pressure wave form information.

2. The fluid injection system of claim 1, wherein the state logic protocol created by the monitoring control module comprises:
 in the event the pressure wave form information is indicative of fluid communication between the at least one fluid path set and the patient's vasculature, instructing the fluid control module to allow the injection procedure, while preventing the purging or priming sequence; and
 in the event the pressure wave form information is indicative of no fluid communication between the at least one fluid path set and the patient's vasculature, instructing the fluid control module to allow the purging or priming sequence.

3. The fluid injection system of claim 1, further comprising a transducer positioned in-line with the at least one fluid path set and operatively connected to the hemodynamic monitoring system,
 wherein the transducer is configured to monitor and convert a fluid flow pressure of the medical fluid within the at least one fluid path set into the electrical signals to be sent to the hemodynamic monitoring system.

4. The fluid injection system of claim 3, wherein the transducer comprises a pressure transducer.

5. The fluid injection system of claim 3, further comprising a hemodynamic monitoring mechanism positioned in-line between the transducer and the hemodynamic monitoring system.

6. The fluid injection system of claim 5, wherein the hemodynamic monitoring mechanism is configured to send pressure wave form information regarding the medical fluid in the at least one fluid path set to the monitoring control module.

7. The fluid injection system of claim 1, wherein the graphical user interface includes a first monitoring control module and the fluid control module includes a second monitoring control module.

8. The fluid injection system of claim 1, further comprising an automatic pressure isolation valve positioned in-line with the at least one fluid path set,
 wherein the automatic pressure isolation valve is configured to control the flow of the medical fluid through the at least one fluid path set.

9. The fluid injection system of claim 1, wherein the graphical user interface is configured to display the pressure wave form information to a user to indicate whether there is a fluctuation in a fluid flow pressure in the at least one fluid path set.

10. The fluid injection system of claim 1, wherein:
 in the event the medical fluid is being directed through the at least one fluid path set to the patient's vasculature, the graphical user display will display a first pressure wave,
 in the event the medical fluid is not being directed through the at least one fluid path set to the patient's vasculature, the graphical user display will display a second pressure wave of substantially zero value, and
 in the event the medical fluid is being directed through the at least one fluid path set with an amount of air, the graphical user display will display a third pressure wave that is smaller than the first pressure wave but greater than the second pressure wave.

11. The fluid injection system of claim 1,
 wherein the graphical user interface is configured to display a visual indicator regarding a status of the system,
 wherein the visual indicator is displayed as a warning indicator when a measured fluid pressure in the at least one fluid path set is greater than or equal to a possible human intra-coronary pressure range,
 wherein the visual indicator is displayed as a caution indicator when the measured fluid pressure in the at least one fluid path set is greater than a normal human intra-coronary pressure range, but less than the possible human intra-coronary pressure range, and
 wherein the visual indicator is displayed as a ready-to-use indicator when the measured fluid pressure in the at least one fluid path set is less than or equal to the normal human intra-coronary pressure range.

12. The fluid injection system of claim 1, further comprising an air detector positioned in-line with the at least one fluid path set.

13. A fluid injection system, comprising:
 a fluid control module;
 a first fluid path set in fluid communication with the fluid control module;
 a second fluid path set in fluid communication with the fluid control module;
 a pressure isolation valve in fluid communication with the first fluid path set and second fluid path set;
 a third fluid path set in fluid communication with the pressure isolation valve and a patient's vasculature; and
 a hemodynamic monitoring system operatively connected to the second fluid path set and the fluid control module,
 wherein the hemodynamic monitoring system is configured to receive electrical signals indicative of pressure waves formed in a medical fluid injected through the second fluid path set based on a location of the third fluid path set in the patient's vasculature, to convert the electrical signals into pressure wave form information, and to send the pressure wave form information to the fluid control module, and wherein based on the pressure wave form information received from the hemodynamic monitoring system, the fluid control module is configured to create a state logic protocol to allow an injection procedure or allow a purging or priming sequence using the fluid control module.

14. The fluid injection system of claim 13, wherein the state logic protocol created by the fluid control module comprises:

in the event the pressure wave form information is indicative of fluid communication between the third fluid path set and the patient's vasculature, instructing the fluid control module to allow the injection procedure, while preventing the purging or priming sequence; and in the event the pressure wave form information is indicative of no fluid communication between the third fluid path set and the patient's vasculature, instructing the fluid control module to allow the purging or priming sequence.

15. The fluid injection system of claim 13, wherein the pressure isolation valve comprises an automatic spring-biased spool valve.

16. The fluid injection system of claim 13, further comprising a transducer positioned in-line with the second fluid path set and operatively connected to the hemodynamic monitoring system, wherein the transducer is configured to monitor and convert a fluid flow pressure of the medical fluid within the second fluid path set into the electrical signals to be sent to the hemodynamic monitoring system.

17. The fluid injection system of claim 16, further comprising a hemodynamic monitoring mechanism positioned in-line between the transducer and the hemodynamic monitoring system.

18. The fluid injection system of claim 13, further comprising an air detector positioned in-line with the third fluid path set.

* * * * *

UNITED STATES PATENT AND TRADEMARK OFFICE
CERTIFICATE OF CORRECTION

| | | |
|---|---|---|
| PATENT NO. | : 11,607,489 B2 | |
| APPLICATION NO. | : 16/613457 | |
| DATED | : March 21, 2023 | |
| INVENTOR(S) | : Callan et al. | |

It is certified that error appears in the above-identified patent and that said Letters Patent is hereby corrected as shown below:

On the Title Page

On Page 3, in item (56), under "OTHER PUBLICATIONS", in Column 2, Line 3, delete "Blook" and insert -- Blood --, therefor.

In the Specification

In Column 1, Line 61, delete "liner" and insert -- linear --, therefor.

In Column 11, Line 21, delete "is and" and insert -- and --, therefor.

In Column 12, Line 40, delete "form" and insert -- from --, therefor.

In Column 19, Line 50, delete "312as" and insert -- 312 as --, therefor.

Signed and Sealed this
Eleventh Day of July, 2023

Katherine Kelly Vidal
*Director of the United States Patent and Trademark Office*